US009084647B2

(12) United States Patent
Suh

(10) Patent No.: US 9,084,647 B2
(45) Date of Patent: Jul. 21, 2015

(54) SCREW WITH ANCHOR FEATURES

(75) Inventor: Sean Suh, Plymouth Meeting, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 200 days.

(21) Appl. No.: 13/271,373

(22) Filed: Oct. 12, 2011

(65) Prior Publication Data

US 2013/0096634 A1    Apr. 18, 2013

(51) Int. Cl.
*A61B 17/86* (2006.01)
*A61B 17/84* (2006.01)
*A61B 17/88* (2006.01)
*A61B 17/70* (2006.01)

(52) U.S. Cl.
CPC ......... *A61B 17/8841* (2013.01); *A61B 17/7097* (2013.01); *A61B 17/844* (2013.01); *A61B 17/864* (2013.01); *A61B 2017/8655* (2013.01)

(58) Field of Classification Search
CPC ............... A61M 16/0833; A61M 16/0816; A61B 17/844; A61B 17/864; A61B 17/7097; A61B 17/7098; A61B 2017/8655
USPC ............. 606/92–94, 86 R, 104, 300, 301, 606/303–316, 318, 323, 326–331; 411/15, 411/19; 128/204.18
See application file for complete search history.

(56) References Cited

U.S. PATENT DOCUMENTS

| | | | | |
|---|---|---|---|---|
| 4,968,306 A | * | 11/1990 | Huss et al. | 604/264 |
| 5,346,495 A | * | 9/1994 | Vargas, III | 606/92 |
| 6,214,012 B1 | * | 4/2001 | Karpman et al. | 606/93 |
| 7,354,442 B2 | * | 4/2008 | Sasso et al. | 606/280 |
| 7,491,236 B2 | * | 2/2009 | Cragg et al. | 623/17.11 |
| 8,951,265 B2 | * | 2/2015 | Schwappach | 606/105 |
| 2003/0083662 A1 | * | 5/2003 | Middleton | 606/72 |
| 2008/0249603 A1 | * | 10/2008 | Schwardt et al. | 623/1.15 |
| 2009/0099609 A1 | * | 4/2009 | Froehlich | 606/301 |

FOREIGN PATENT DOCUMENTS

JP    8038618    *    2/1996

* cited by examiner

*Primary Examiner* — Todd Manahan
*Assistant Examiner* — Marcela I Shirsat

(57) ABSTRACT

Screws for anchoring in cancellous or other low-quality bone are described. One type of screw addresses the problem of extravazation of bone cement when filling an area of low-quality bone. The screw includes an expandable container for retaining bone cement and anchoring the screw in low-quality bone. The screw also includes an anchoring device for holding the screw in place in the bone while it is supplied with bone cement or other appropriate filler. The screw further includes a head for connecting to a rod or other apparatus. A second type of screw uses an expandable container to deform two or more fins to compress cancellous bone and/or anchor in cancellous bone.

10 Claims, 4 Drawing Sheets

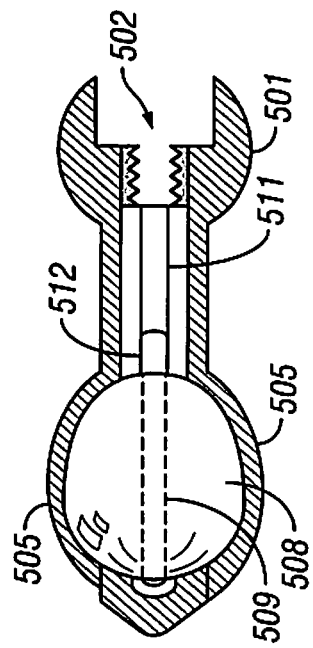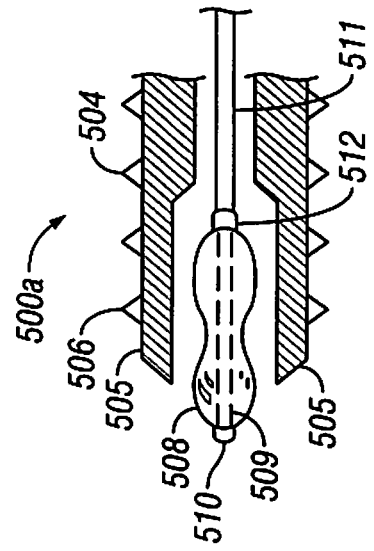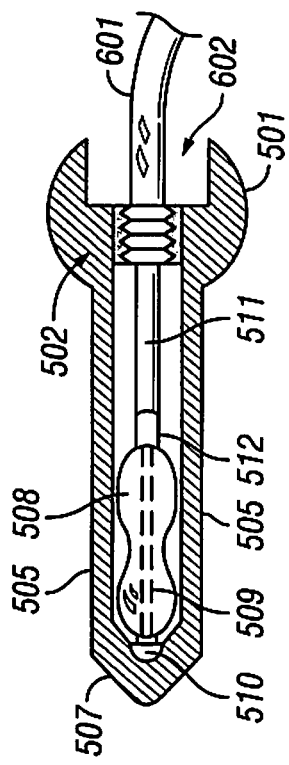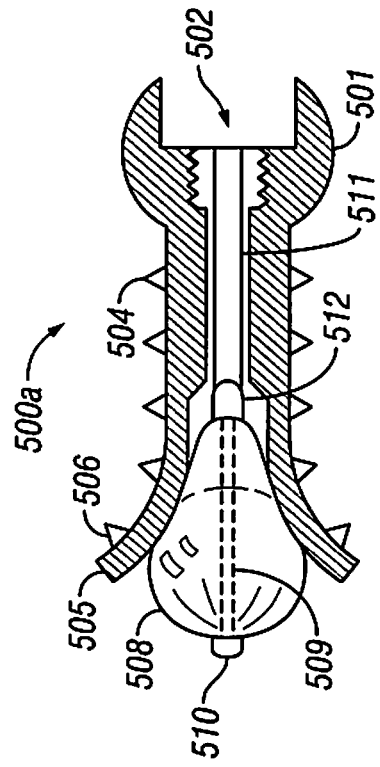

SCREW WITH ANCHOR FEATURES

BACKGROUND OF THE DISCLOSURE

1. Field of the Disclosure

The disclosure is directed to bone screws with anchor features for securely attaching to low-quality cancellous bone, such as may be found, for example, in a vertebral body of a patient with osteoporosis.

2. Related Art

Pedicle screws are commonly used to attach a spinal fusion apparatus to a patient's spine. The screws are bored through cortical bone of the pedicle and place their distal portion in the cancellous bone of the vertebral body. The portion of the screw anchored in cancellous bone may be as much as 50%. The quality of the cancellous bone is therefore critical for the overall stability of the apparatus, as well as the success of the fusion process.

Several factors may reduce the quality of the cancellous bone. The patient's age is the most common factor. Diseases and injuries, such as, e.g., osteoporosis and vertical compression fractures, can further reduce the bone quality.

In patients with low-quality cancellous bone, the common solution is to fill the vertebral body with bone cement. This solution, however, may be inadequate due to extravasation of the bone cement. In addition, low-quality cortical bone on the outside of the vertebral body may not retain all of bone cement.

Accordingly, there is a need for pedicle screws that retain bone cement or provide alternative means of anchoring in low-quality bone.

SUMMARY OF THE DISCLOSURE

The disclosure meets the foregoing need and allows pedicle screws to anchor in low-quality cancellous bone using an expandable container, which results in a significant increase in the strength of bone-screw interface and the overall anchorage of the screw, as well as other advantages apparent from the discussion herein.

According to one aspect of the invention, a screw for anchoring in cancellous bone includes a screw head including a receiver, a distal end, and a proximal end, the proximal end configured as a channel, an anchoring device connected to the distal end of the screw head, an expandable container, and a neck connected to the temporary anchoring device and to the expandable container.

According to another aspect of the invention, a screw for anchoring in cancellous bone includes a body including bone threads, a proximal end, and a distal end, a head connected to the proximal end of the body, the head including a receiver, a plurality of fins connected to the distal end of the body, the plurality of fins defining an interior space, and an expandable container located in the interior space.

Accordingly, one aspect of the disclosure describes a screw for anchoring in cancellous or other low-quality bone. The screw includes a screw head with a receiver, a proximal end and a distal end. The proximal end of the screw head is structured to accept a lumen. A temporary anchoring device is connected to the distal end of the screw head. The screw also includes an expandable container and a neck connecting the temporary anchoring device to the expandable container.

A delivery adapter may be provided for connecting to the screw. The delivery adapter may include a body with a proximal end and a distal end. A connector for connecting to the screw's receiver may be attached to the distal end of the body. The delivery adapter may also include a filler arm connected to the body.

The temporary anchoring device may include bone threads. The receiver may include female threads. The screw itself may also include a lumen from the receiver to the distal end of the expandable container, as well as a filler space from the receiver to the expandable container. The filler space may be in fluid communication with the expandable container and separate and distinct from the lumen.

A delivery adapter may be provided for connecting to the screw. The delivery adapter may include a body with a proximal end and a distal end. A connector for connecting to the screw's receiver may be attached to the distal end of the body. A stylet port may be located on the proximal end of the body. A lumen may connect the stylet port to the connector, and the lumen may be configured to connect to the lumen of the screw. The delivery adapter may also include a filler arm, with both a proximal end and a distal end, connected to the body at the distal end of the filler arm. A filler port may be connected to the proximal end of the filler arm. A filler space, separate and distinct from the lumen, may connect the filler port to the connector. The filler space may be configured to connect to the filler space of the screw at the connector.

According to another aspect of the disclosure, a screw for anchoring in cancellous or other low-quality bone includes a body with bone threads, a proximal end, and a distal end. A screw head, which includes a receiver, is connected to the proximal end of the body. Two or more fins are connected to the distal end of the body and define an interior space. An expandable container is located in the interior space.

The head of the screw may be structured to accept a polyaxial connector, a monoaxial connector, a fixed connector, or any combination thereof. The screw may also include a screw tip connected to the distal end of one or more fins. The fins may include bone threads. The receiver may be structured to connect to a fluid source and receive a pressurized fluid, which may be saline, polymethyl methacrylate (PMMA), or any other appropriate gas or liquid. The screw may include a channel structured and arranged to convey the pressurized fluid from the receiver to the expandable container. The expandable container may be expanded by the pressurized fluid. The expansion of the container may cause the deformation of one or more of the fins.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate aspects of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 6A shows a cutaway view of the screw of FIG. 5A with the fins in a straight position and a collapsed container;

FIG. 6B shows a cutaway view of the screw of FIG. 5A with the container expanded and the fins in a deformed configuration;

FIG. 7A shows a screw that is constructed without a tip; and

FIG. 7B shows the distal end of the screw of FIG. 7A with the container in a collapsed position and the fins in a straight configuration.

DETAILED DESCRIPTION OF THE DISCLOSURE

Figure 1:
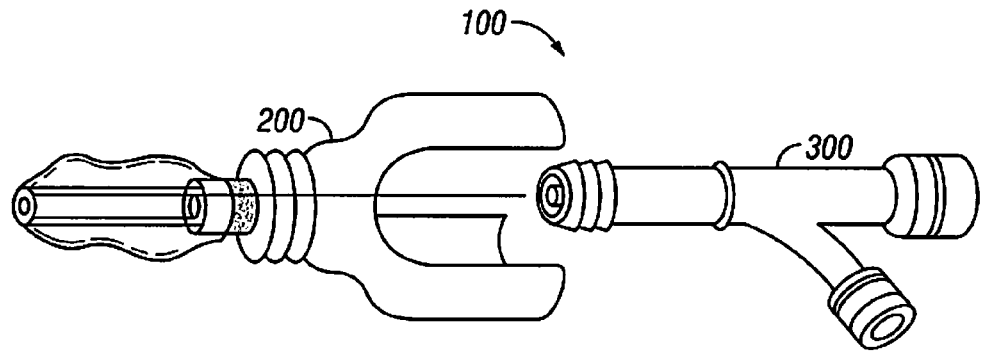
FIG. 1 shows a screw with containment features and a delivery adapter, according to an aspect of the disclosure.

The aspects of the disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the disclosure. The examples used herein are intended merely to facilitate an understanding of ways in which the disclosure may be practiced and to further enable those of skill in the art to practice the aspects of the disclosure. Accordingly, the examples and aspects herein should not be construed as limiting the scope of the disclosure, which is defined solely by the appended claims and applicable law. Moreover, it is noted that like reference numerals represent similar parts throughout the several views of the drawings.

Figure 2:
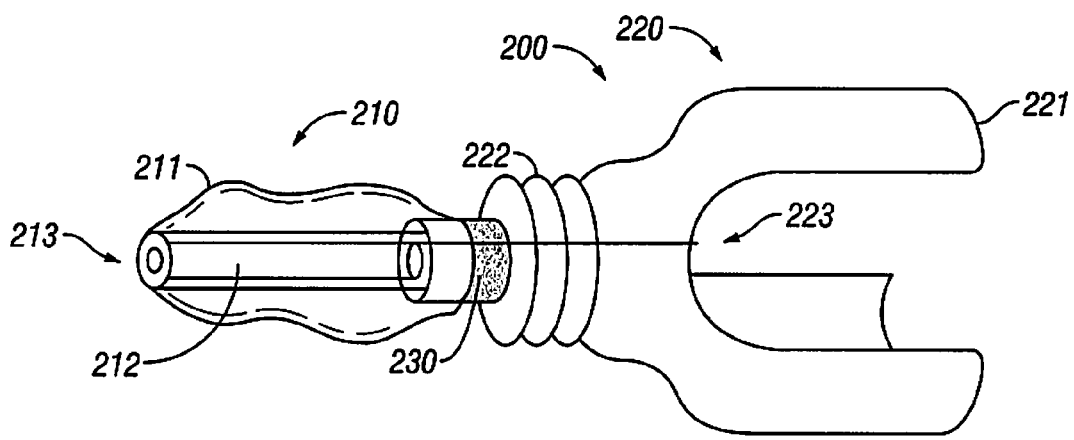
FIG. 2 shows the screw of FIG. 1 without the delivery adapter.

FIG. 1 shows a screw with containment features 100, according to an aspect of the disclosure. The screw with containment features 100 may include two main components, a screw 200 and a filler delivery adapter 300. As seen in FIG. 2, the screw 200 may be further divided into a distal portion 210 and a proximal portion 220, connected by a neck 230.

FIG. 2 further shows the screw 200 according to an aspect of the disclosure. The distal portion 210 of the screw 200 may include an expandable container 211 attached to the neck 230. The distal portion 210 may also include an inner lumen 212 through the container 211. The lumen 212 may be sealed against the container 211, defining a separate space. The lumen 212 may be connected to a distal port 213.

The neck may be connected to the proximal portion 220 of the screw 200. More specifically, the neck 230 may be connected to a temporary anchoring device (TAD) 222. The TAD 222 may serve to temporarily anchor the screw to the bone prior to filling the container 211 with bone cement or other suitable compound. The TAD 222 may include bone threads or any other device suitable construction for temporarily anchoring the screw 100 in the bone, as will be understood by one skilled in the art. The proximal portion may also include a screw head 221. The screw head 221 may provide an appropriate interface for connecting the screw 200 to a rod or other device (not shown). The interface may be, for example, a polyaxial connector, a monoaxial connector, or a fixed connector. Other connector types are contemplated and may be used without departing from the spirit and scope of the specification and the claims. The proximal portion 220 may further include a receiver 223 for connecting to a delivery adapter.

Figure 3:
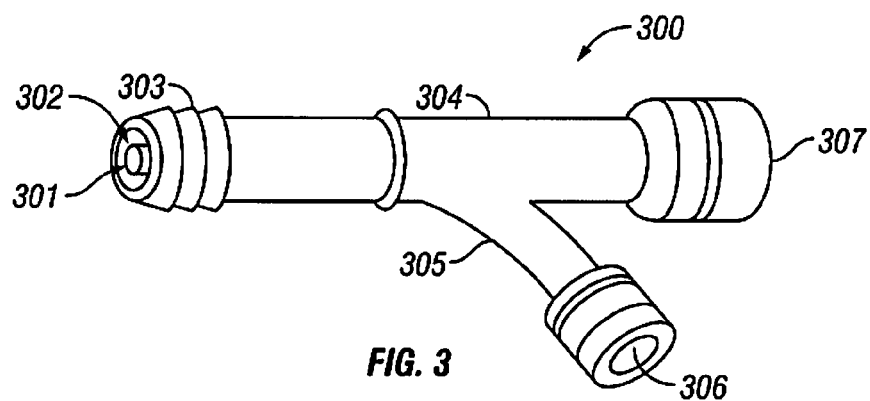
FIG. 3 shows the delivery adapter of FIG. 1.

FIG. 3 shows a filler delivery adapter 300, according to an aspect of the disclosure. The delivery adapter 300 may include a body 304 that interfaces with the screw 200 at the body's distal end. In particular, the body may include a connector 303 that removable attaches to the receiver 223 on the screw. The distal end of the adapter 300 may provide an interface lumen port 301, which may connect to the lumen of the screw, and an interface filler port 302, which may connect to the filler space of the screw. The proximal end of the adapter 300 may include a stylet port 307, which may connect to the lumen of the delivery adapter 300 and, in turn, the interface lumen port 301. The delivery adapter 300 may also include a filler arm 305, which may end in a filler port 306.

Figure 4:
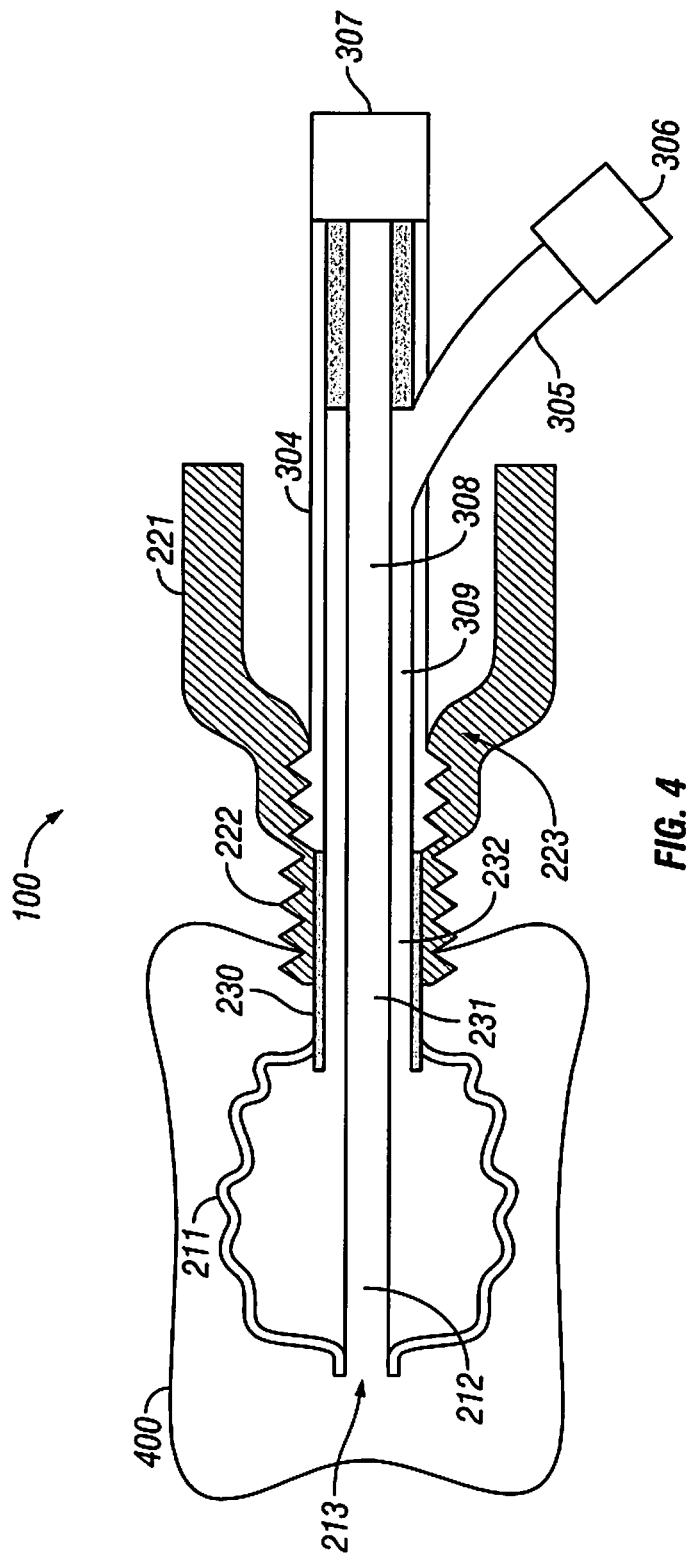
FIG. 4 shows a cutaway view of the assembled screw with containment features of FIG. 1 attached to a bone, such as a vertebra.

FIG. 4 shows a cutaway view of the assembled screw with containment features 100 attached to a bone 400, such as a vertebra. In the fully assembled device, the inner lumen 212, lumen space 231, and inner lumen 308 may form a continuous space, which may allow, e.g., a straight instrument to be passed through the screw 100 to the bone on the distal side. Stylet port 307 may provide access to the lumen on the proximal end, and distal port 213 may provide access to the lumen on the distal end.

Similarly, filler space 309 and filler space 232 may connect filler port 306 to container 211. A supply of filler (not shown) may be connected to filler port 306 and may be provided to the container 211 under pressure. As the filler enters the container 211, the container 211 may expand and compress cancellous bone in the surrounding vertebral body or other bone 400. Expansion of the container 211, which may be accompanied by solidification of the filler, may create a solid, stable anchor for the screw 100 in low-quality cancellous bone. The container 211 itself may prevent extravasation of the filler, further enhancing the stability of the anchor. In one aspect of the disclosure, the filler may be bone cement, also known as polymethyl methacrylate (PMMA). Other suitable compounds may be used, as will be understood by one skilled in the art, without departing from the spirit and scope of the specification or the claims.

The screw with containment features 100 may be temporarily anchored to the bone 400 with temporary anchoring device (TAD) 222. For aspects of the disclosure where the TAD includes bone threads, a pilot hole may be drilled in the bone 400. The pilot hole may be deep enough into the bone to additionally accommodate neck 230 and distal portion 210.

Delivery adapter 300 may attach to screw 200 at an interface. In certain aspects of the disclosure, the interface may include male threads on the distal portion of the filler adapter and corresponding female threads in the proximal portion 220 of the screw 200. The interface may also align lumen space 231 with inner lumen 308, as well as filler space 232 with filler space 309. The corresponding sections may be in fluid communication with one another but not with the other sections. In other words, lumen space 231 and inner lumen 308 may form a continuous space that is not in fluid communication with the continuous space formed by filler space 232 and filler space 309.

Figure 5A:
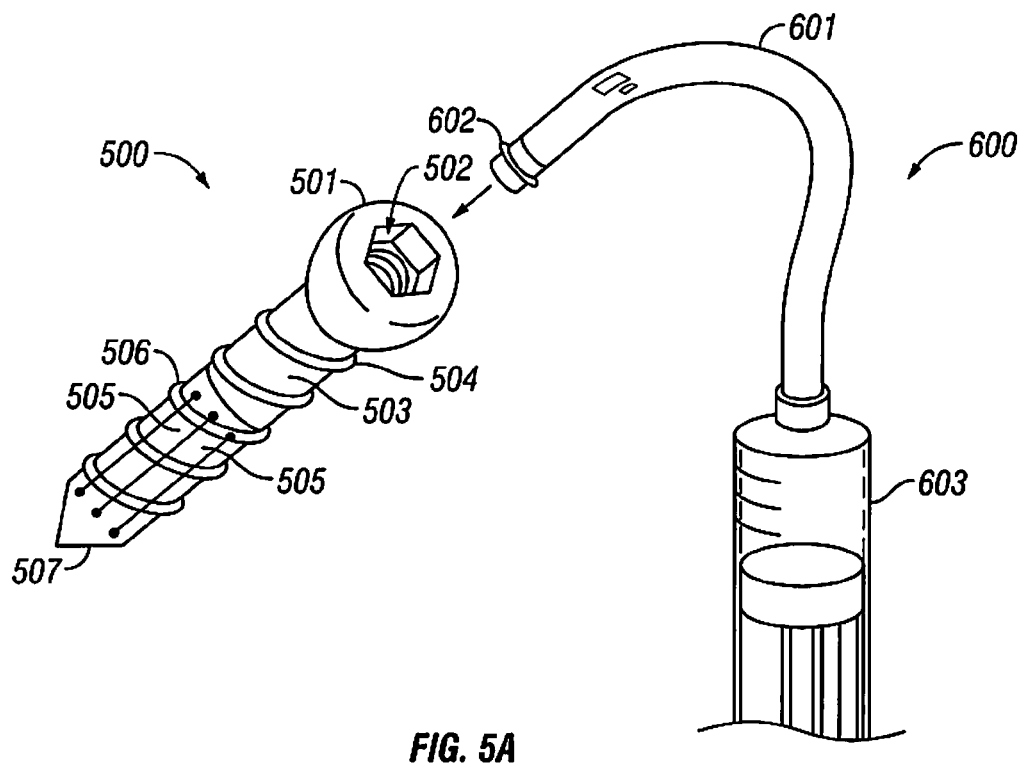
FIG. 5A shows an expanding screw, according to an additional aspect of the disclosure.

FIG. 5A shows an expanding screw, according to an additional aspect of the disclosure. Expanding screws may also be used to anchor a spinal fusion apparatus in low-quality cancellous bone. Expanding screw 500 may include a head 501 that may be used with, e.g., a polyaxial connector, a monoaxial connector, or a fixed connector for attaching to a rod.

Other connector types are contemplated and may be used without departing from the spirit and scope of the specification and the claims.

The head 501 may also provide a receiver 502 for a fluid source 600. Fluid source 600 may include a reservoir 603, a connector 602 for attaching to the receiver 502, and a tube 601 connecting the connector 602 to the reservoir 603. Reservoir 603 may provide a fluid under pressure to connector 602. Reservoir 603 may pressurize the fluid through any appropriate means, as will be understood by one skilled in the art. Examples include a syringe and a mechanical compressor. The reservoir 603 may be manual, mechanical, or powered.

The body 503 of the screw 500 may include one or more bone threads 504. The bone threads 504 may be continuous with bone threads 506 associated with a plurality of fins 505, which may be located distal of the screw body 503. The distal end of screw 500 may terminate in a screw tip 507.

Figure 5B:
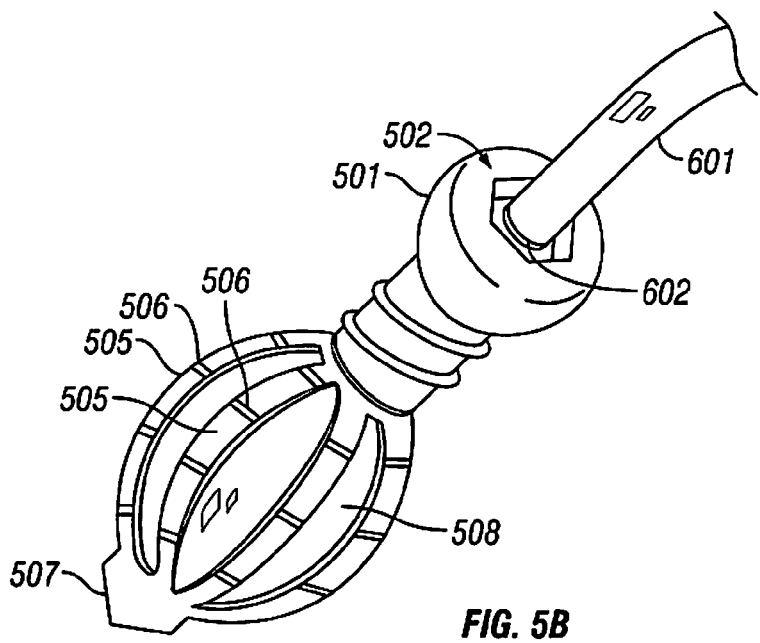
FIG. 5B shows the screw of FIG. 5A after the container has been filled from a fluid source.

FIG. 5B shows the screw 500 after container 508 has been filled from fluid source 600. Connector 602 may be attached to receiver 502, and a fluid from reservoir 603 may be supplied to container 508 under pressure. Expansion of container 508 may cause fins 505 to change shape or deform, assuming a more curved or spherical shape. Container 508 may push fins 505 outward into, e.g., cancellous bone inside a vertebral body. Compression of the cancellous bone may provide fins 505 greater purchase than the fins 505 may have had in non-compressed bone. Bone threads 506, located on fins 505, may further provide increased purchase.

Screw 500, and fins 505 in particular, may be constructed from a material that will retain its altered or expanded shape, even when pressure is withdrawn from container 508. Accordingly, container 508 may be filled with, e.g., saline, which may be drained from the container after the fins 505 have been expanded. Alternatively, container 508 may be filled with, e.g., bone cement (PMMA), which would provide an enlarged anchor as well as additional retention in low-quality bone provided by threads 506.

FIG. 6A shows a cutaway view of the screw 500 with the fins 505 in a straight position and a collapsed container 508. Connector 602 may be attached to receiver 502 to supply a pressurized fluid to the screw 500. From the receiver 502, the fluid may travel along channel 511 to container 508. A fitting 512 may connect the channel 511 to the container 508. A spacer 509 may be disposed within the container 508. The spacer 509 and/or container 508 may terminate in a knob 510 located near the tip 507 of the screw 500.

The spacer 509 may be constructed of a rigid material and may serve to help keep tip 507 at a fixed distance from screw head 501 while fins 505 are undergoing deformation as a result of the expansion of the container 508. Without spacer 509 in place, expansion of the container 508 and deformation of fins 505 may tend to draw tip 507 and screw head 501 closer together. This contracting of the screw 500 may weaken the integrity of the bone-screw interface, thus reducing the strength of the anchor in the bone. For example, contracting the screw may cause the grooves of the bone threads to widen, allowing the screw to wiggle or pivot in the bone.

FIG. 6B shows a cutaway view of the screw 500 with the container 508 expanded and the fins 505 in a deformed configuration. As described above, spacer 509 may keep the screw at a single length during expansion of the container 508 and deformation of the fins 505. To accommodate their increased length, the fins 505 may become thinner, as seen in FIG. 6B.

Screw 500 may be shipped in a pre-assembled format, with the expansion apparatus, which may include knob 510, container 508, fitting 512, channel 511, and receiver 502, already inserted into the screw or integrally formed therein. Alternatively, the expansion apparatus may be reusable, which may reduce the cost of the device. According to this aspect, the expansion apparatus maybe inserted into the screw housing through an aperture in the screw head 501. Once the container 508 has been filled, the fluid is allowed to drain, either naturally or with mechanical assistance, and the expansion apparatus is removed for use with another screw.

FIG. 7A shows a screw 500a that is constructed without a tip 507. As the screw 500a may be inserted into a pre-drilled hole, the tip 507 may not be necessary to successfully attach the screw to a bone. Without a tip to hold the fins 505 together at the distal end, the deformed fins may assume a more convex shape, rather than the curved or spherical shape seen in previous aspects. Space 509 and knob 510 may still be present in this aspect. Here, they may serve to control or guide expansion of the container 508.

FIG. 7B shows the distal end of the screw 500a with the container in a collapsed position and the fins 505 in a straight configuration. As screw 500a is open on its distal end, it may be assembled from the distal end. The expansion apparatus, which may include knob 510, container 508, fitting 512, channel 511, and receiver 502, may be inserted through the aperture created by the removal of the screw tip.

While the disclosure has been described in terms of exemplary aspects, those skilled in the art will recognize that the disclosure can be practiced with modifications in the spirit and scope of the appended claims. These examples given above are merely illustrative and are not meant to be an exhaustive list of all possible designs, aspects, applications or modifications of the disclosure.

What is claimed is:

1. A screw for anchoring in cancellous bone, the screw comprising:
   a screw head comprising a receiver, a distal end, and a proximal end, wherein the proximal end is configured as a channel;
   an anchoring device connected to the distal end of the screw head;
   an expandable container;
   a delivery adapter, the delivery adapter comprising:
      a body comprising a proximal end and a distal end;
      a connector attached to the distal end of the body, wherein the connector is configured to be removably attached to the receiver of the screw head,
      wherein the connector comprises a lumen port and an interface filler port that coaxially surrounds the lumen port; and
      a filler arm connected to the body; and
   an inner lumen extending through the expandable container, wherein the inner lumen forms an opening at a distal most end of the screw,
   wherein the lumen port of the connector is configured to interface with the inner lumen of the screw and the interface filler port connects to filler space around the inner lumen of the screw.

2. The screw of claim 1, wherein the anchoring device comprises bone threads.

3. The screw of claim 1, wherein the receiver comprises female threads.

4. The screw of claim 1, further comprising:
   wherein the inner lumen extends from the receiver to a distal end of the expandable container; and
   wherein the screw further comprises a filler space from the receiver to the expandable container, the filler space in fluid communication with the expandable container, the filler space separate and distinct from the inner lumen.

5. The screw of claim 1, wherein the inner lumen is completely sealed against the expandable container.

6. The screw of claim 1, wherein a distal end of the connector comprises threaded features that engage with inner threads of the screw head.

7. The screw of claim 1, wherein the delivery adaptor comprises a stylet port for connecting to a delivery adapter.

8. The screw of claim 7, wherein the delivery adaptor comprises a filler port for connecting to a delivery adapter.

9. The screw of claim 8, wherein the filler port is at an angle to the stylet port.

10. The screw of claim 1, further comprising a neck connected to the anchoring device and to the expandable container.

* * * * *